US00PP35322P2

(12) United States Plant Patent
Gerits

(10) Patent No.: US PP35,322 P2
(45) Date of Patent: Aug. 15, 2023

(54) ***ECHINACEA* PLANT NAMED 'PEECHPANGO'**

(50) Latin Name: *Echinacea purpurea*
Varietal Denomination: PEECHPANGO

(71) Applicant: Perennial Green GmbH, Kempen (DE)

(72) Inventor: Werner Gerits, Kempen (DE)

(73) Assignee: Perennial Green GMBH

( * ) Notice: Subject to any disclaimer, the term of this patent is extended or adjusted under 35 U.S.C. 154(b) by 0 days.

(21) Appl. No.: 18/074,917

(22) Filed: Dec. 5, 2022

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

(56) References Cited

PUBLICATIONS

CPVO Register—CPVO Application Consultation version 4.4.9 for *Echinacea* 'PEECHPANGO'; Mar. 6, 2023; 3 pages.*

* cited by examiner

*Primary Examiner* — Kent L Bell
(74) *Attorney, Agent, or Firm* — Cassandra Bright

(57) ABSTRACT

A new and distinct cultivar of *Echinacea purpurea* plant named 'PEECHPANGO' is disclosed, characterized by ray florets typically colored bright orange. The bright orange ray floret coloration resists fading with age. Inflorescences bloom early and over a long period, from June to November. *Echinacea* is a popular genus, typically used as container plants or landscape plants.

2 Drawing Sheets

Latin name of the genus and species: *Echinacea purpurea.*

Variety denomination: 'PEECHPANGO'.

BACKGROUND OF THE INVENTION

The new variety, *Echinacea* 'PEECHPANGO', is the product of a planned breeding program by the inventor. The crossing resulting in the new variety was made during June of 2018 at a home nursery in Kempen, Germany. The seed parent is the unpatented proprietary variety of *Echinacea purpurea* referred to as 'ES18-01-11'. The pollen parent is the unpatented proprietary variety of *Echinacea purpurea* referred to as 'ES18-01-06'. The discovery was made during June of 2019, in Kempen, Germany, at the inventor's home nursery.

Asexual reproduction of the new variety 'PEECHPANGO' was first performed in Kempen, Germany, at the same home nursery, by terminal vegetative cuttings in August of 2019. *Echinacea* 'PEECHPANGO' has since produced at least three generations and has shown that the unique features of this variety are stable and reproduced true to type.

The first offer for sale occurred Jan. 16, 2022 in Germany. This sale was made by Perennial Green GmbH who obtained the claimed invention directly from the Inventor. This sale falls within the exception allowed under 35 U.S.C. 102(b)(1).

SUMMARY OF THE INVENTION

The variety 'PEECHPANGO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PEECHPANGO'. These characteristics in combination distinguish 'PEECHPANGO' as a new and distinct *Echinacea* variety:

1. Early and long blooming period (from June to November).
2. Basal branching.
3. Bright orange color of ray florets (Near RHS Orange N25B).
4. Keeps color at fading (Near RHS Orange N25D).
5. Successful propagation through vegetative cuttings.

PARENTAL COMPARISON

Plants of the new variety 'PEECHPANGO' are similar to plants of the seed parent in most horticultural characteristics. However, plants of the new variety 'PEECHPANGO' differ in the following:

1. Ray florets of the new variety are a stronger orange color than ray florets of the seed parent.
2. Inflorescences of the new variety are larger than inflorescences of the seed parent.

Plants of the new variety 'PEECHPANGO' are similar to plants of the pollen parent in most horticultural characteristics. However, plants of the new variety 'PEECHPANGO' differ in the following:

1. Ray floret color of the new variety is bright orange while the ray floret color of the pollen parent is light yellow.

2. Plants of the new variety have basal branching, while plants of pollen parent have no basal branching.

COMMERCIAL COMPARISON

The new variety 'PEECHPANGO' can be compared to the commercial variety *Echinacea* 'Apecssiye', U.S. Plant Pat. No. 28,827. Plants of the new variety 'PEECHPANGO' differ in the following:

1. Plants of the new variety are about 32 cm in height, while plants of this comparator are about 25 cm in height.
2. Ray floret color of the new variety is bright orange, while the ray floret color of this comparator is a lighter yellow.
3. Ray florets of this comparator have a stronger loss of color at fading than ray florets of the new variety.
4. Ray florets of the new variety are fewer and longer than ray florets of this comparator.
5. Leaves of this comparator are darker green and narrower than leaves of the new variety.

The new variety 'PEECHPANGO' can be compared to *Echinacea* 'Balsomemy', U.S. Plant Pat. No. 24,768. Plants of the new variety 'PEECHPANGO' differ in the following:

1. Plants of the new variety are about 32 cm in height, while plants of this comparator are about 20 cm in height.
2. The blooming period of the new variety is June until November, while the blooming period of this comparator is July until September.
3. Ray floret color of the new variety is bright orange; ray floret color of this comparator is bright yellow.
4. Ray florets of the new variety hang down on mature inflorescence, while ray florets of this comparator stay straight at fading.
5. Leaves of the new variety are wider than leaves of this comparator.

BRIEF DESCRIPTION OF THE PHOTOGRAPHS

The photographs were taken using conventional techniques and equipment. While the colors in these photographs may display variances of color as compared to the living variety, due to LRV (light reflectance value), they are as accurate as possible using conventional photographic techniques. Colors in the photographs may appear to differ slightly from the color values cited in the botanical description, which accurately describe the colors of new *Echinacea* 'PEECHPANGO'. Plants were grown in Kempen, Germany.

DETAILED BOTANICAL DESCRIPTION

Figure 1:
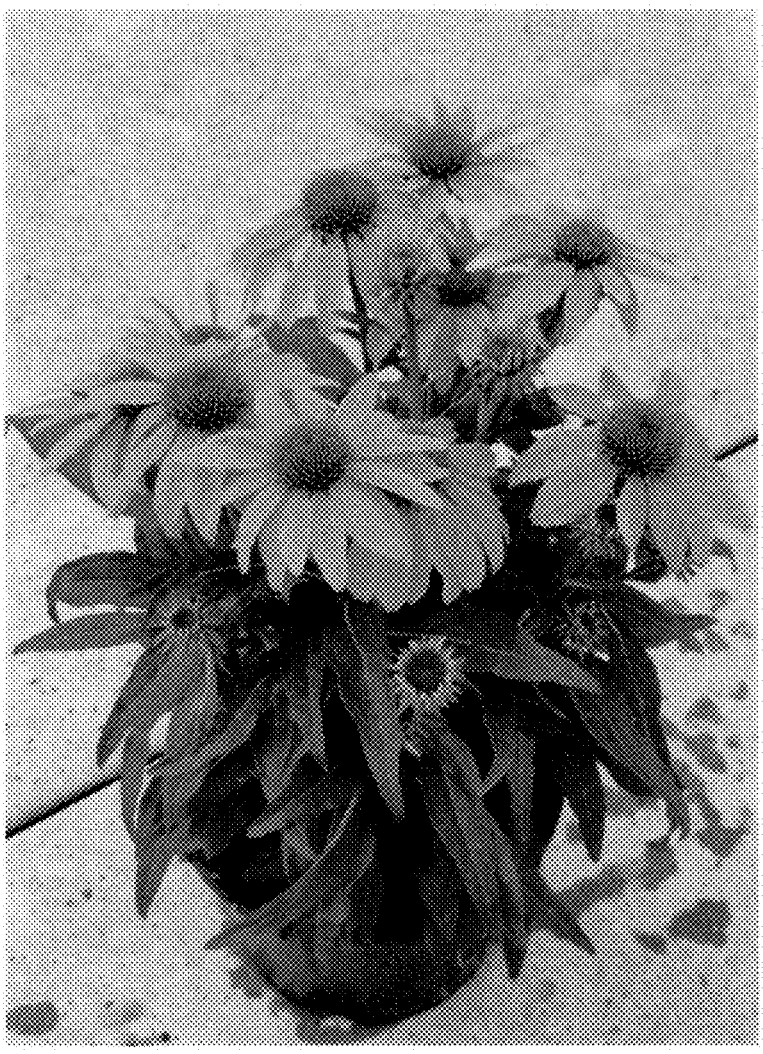
FIG. 1 illustrates in full color a plant of *Echinacea* 'PEECHPANGO' grown in a 2 liter pot at approximately 1 year old.
Figure 2:
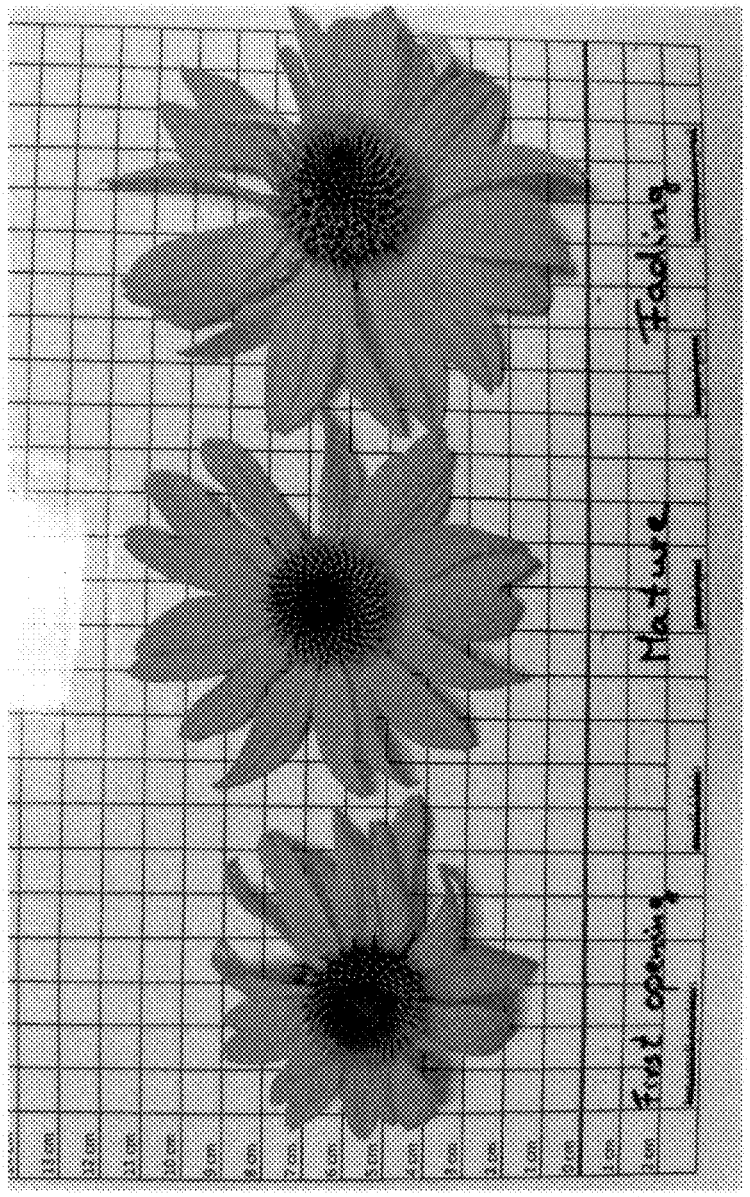
FIG. 2 illustrates in full color a comparison of the inflorescences of *Echinacea* 'PEECHPANGO' at different stages of maturity.

In the following description, color references are made to The Royal Horticultural Society Colour Chart, 2007, except where general terms of ordinary dictionary significance are used. The following observations and measurements describe 'PEECHPANGO' plants grown outdoors in Kempen, Germany. Measurements and numerical values represent averages of typical plant types.

Botanical classification: *Echinacea purpurea* 'PEECHPANGO'.

PROPAGATION

Time to rooting: 15 to 20 days at approximately 18° to 22° C.

Time to produce a rooted cutting: Approximately 12 weeks.

Root description: Fibrous and branched. Young roots white, older roots creamy brown. Colors not accurately measured with R.H.S. Chart.

PLANT

Growth habit: Hardy, upright, herbaceous perennial.

Blooming period: Naturally blooming June to November (Kempen, Germany).

Height: Approximately 32 cm.

Plant spread: Approximately 32 cm.

Growth rate: Moderate.

Branching characteristics: Porrect, alternate.

Length of lateral branches: Approximately 21 cm.

Diameter of lateral branches: Approximately 0.3 cm.

Quantity of lateral branches: Approximately 3.

Texture of lateral branches: Hispid. Hair color: Near RHS White 155A.

Color of lateral branches: Near RHS Yellow Green 149B.

Aspect: Approximately 20° from base of plant (vertical).

Internode length: Approximately 4.5 cm (lateral branches mostly grow from ground level).

Number of leaves per lateral branch: Approximately 6.

Age of plant described: Approximately 9 months from a rooted cutting.

FOLIAGE

Leaf:

*Arrangement*.—Alternate, simple.

*Average length*.—Smallest apical leaves approximately 5 cm. Largest basal leaves approximately 9 cm.

*Average width*.—Smallest apical leaves approximately 1.1 cm. Largest basal leaves approximately 4.1 cm.

*Shape of blade*.—Narrowly ovate to lanceolate.

*Apex*.—Acute.

*Base*.—Lateral leaves: attenuate, fused to petiole; basal leaves: cordate to attenuate, fused to petiole.

*Attachment*.—Sessile, fused.

*Margin*.—Finely serrate.

*Texture of top surface*.—Moderately hispid.

*Texture of bottom surface*.—Moderately hispid.

*Leaf internode length*.—Approximately 3 cm on stems. Basal leaves grow from ground level.

*Color*.—Young foliage upper side: Near RHS Green 137A. Young foliage under side: Near RHS Green 137B. Mature foliage upper side: Near RHS Green NN137A. Mature foliage under side: Near RHS Green NN137B.

*Venation*.—Type: Pinnate. Venation color upper side: Near RHS Yellow-Green 144D. Venation color under side: Near RHS Yellow-Green 144D.

Petiole: Basal leaves only.

*Length*.—Approximately 9.2 cm.

*Diameter*.—Approximately 0.2 cm.

*Texture*.—Glabrous near base, becoming sparsely pubescent near leaf blade.

*Color*.—Near RHS Green 143C.

FLOWER

Blooming period: Naturally blooming June to November (Kempen, Germany).

Bud:
- *Bud shape*.—Oblate globular.
- *Bud length*.—Approximately 1 cm.
- *Bud diameter*.—Approximately 1.2 cm.
- *Bud color*.—Near RHS Green 143C.

Inflorescence:
- *Form*.—Composite, held terminally on strong peduncle. Borne singly.
- *Diameter of entire inflorescence*.—Approximately 10 cm.
- *Depth of inflorescence*.—Approximately 2.3 cm.
- *Disc diameter*.—Approximately 2.8 cm.
- *Disc type*.—Daisy.
- *Disc height*.—About 1.5 cm.
- *Receptacle shape*.—Conical.
- *Receptacle height*.—Average 0.6 cm.
- *Receptacle diameter*.—Average 1.7 cm.
- *Quantity of inflorescences per lateral stem*.—1.
- *Quantity of open inflorescences and buds per plant*.—Average 20.
- *Longevity*.—Approximately 20 days.
- *Rate of opening*.—3 to 5 days from bud to fully opened flower.
- *Persistent or self-cleaning*.—Persistent.

Ray florets:
- *Arrangement*.—Rotationally symmetric.
- *Aspect/orientation*.—Showing down from the level of disc, subtending with age in mature flower.
- *Shape*.—Narrowly oblanceolate.
- *Number of ray florets*.—Average 17.
- *Length*.—Approximately 4.2 cm.
- *Width*.—Approximately 1.3 cm.
- *Apex shape*.—Incised with two acute tips.
- *Base*.—Attenuate.
- *Margin*.—Entire.
- *Texture*.—Smooth, ribbed longitudinally.
- *Color*.—Upper surface at first opening: Near RHS Orange N25C. Upper surface at maturity: Near RHS Orange N25B. Upper surface at fading: Near RHS Orange N25D. Under surface at first opening: Near RHS Yellow 7D. Under surface at maturity: Near RHS Yellow-Orange 16D. Under surface at fading: Near RHS Yellow 13D.

Disc florets:
- *Number of disc florets*.—Approximately 200.
- *Arrangement*.—Spirally arranged in center of each inflorescence.
- *Length*.—Approximately 0.8 cm.
- *Width*.—Approximately 1.75 mm.
- *Shape*.—Tubular.
- *Margin*.—Entire.
- *Apex*.—Five acute tips.
- *Base*.—Fused into tube.
- *Texture*.—Glabrous, glossy.
- *Receptacle spines*.—Number of spines per disc floret: 1. Spine shape: Cylindrical with conical tips. Spine apex: Acute. Spine texture: Glabrous, glossy. Spine apex color: Near RHS Yellow-Orange 17A. Spine mid-section color: Near Green 143C. Spine base color: Near RHS Green 143D.
- *Color*.—At first opening: Near RHS Yellow Green 144B. At maturity: Near RHS Yellow Green N144D.

Fragrance: Faint, sweet.

Phyllaries/involucral bracts:
- *Arrangement*.—Three whorls.
- *Number*.—Approximately 45.
- *Length*.—Approximately 1 cm.
- *Width*.—Approximately 0.25 cm.
- *Shape*.—Narrowly ovate to lanceolate.
- *Apex*.—Acute.
- *Base*.—Truncate.
- *Margin*.—Entire, hispid.
- *Texture*.—Glabrous.
- *Color*.—Inside color: Near RHS Green 143C. Outside color. Near RHS Green 137C.

Peduncle:
- *Length*.—Average 28 cm.
- *Width*.—Average 0.45 cm.
- *Texture*.—Moderately hispid.
- *Color*.—Near RHS Yellow Green 145B.

REPRODUCTIVE ORGANS

Androecium:
- *Stamens per disc floret*.—5.
- *Filament length*.—Approximately 0.2 cm.
- *Filament color*.—Near RHS Yellow Green 145D.
- *Anther shape*.—Oblong.
- *Anther length*.—About 0.3 cm.
- *Anther color*.—Near RHS Brown N200A.
- *Pollen amount*.—Abundant.
- *Pollen color*.—Near RHS Yellow 13B.

Gynoecium:
- *Pistil length*.—Approximately 0.8 cm.
- *Stigma shape*.—Decurrent.
- *Stigma color*.—Near RHS Yellow-Green 151B.
- *Style length*.—About 0.5 cm.
- *Style color*.—Near RHS Yellow Green 145C.
- *Ovary color*.—Near RHS Yellow Green 145D.

OTHER CHARACTERISTICS

Fruits and seeds: Fertile, some seed set. Seeds achene, about 3 to 5 mm long and about 2 mm wide. Colored from RHS Yellowish White 158C to Light Yellowish Brown 199C.

Temperature tolerance: Hardy perennial to minus 20° C. Upper temperature tolerance to at least 45° C.

Disease/pest resistance: Neither resistance nor susceptibility to normal diseases and pests of *Echinacea* has been observed.

Drought tolerance: Some drought tolerance, established plants can tolerate infrequent summer watering.

What is claimed is:

1. A new and distinct cultivar of *Echinacea* plant named 'PEECHPANGO' as herein illustrated and described.

* * * * *